(12) United States Patent
Bourrie et al.

(10) Patent No.: US 7,524,857 B2
(45) Date of Patent: *Apr. 28, 2009

(54) PHARMACEUTICAL COMBINATIONS BASED ON PYRIDOINDOLONE DERIVATIVES AND ANTICANCER AGENTS

(75) Inventors: Bernard Bourrie, Saint-Gely-du-Fesc (FR); Pierre Casellas, Montpellier (FR); Jean-Marie Derocq, Murviel-les-Montpellier (FR)

(73) Assignee: Sanofi-Aventis, Paris (FR)

( * ) Notice: Subject to any disclaimer, the term of this patent is extended or adjusted under 35 U.S.C. 154(b) by 914 days.

This patent is subject to a terminal disclaimer.

(21) Appl. No.: 10/476,321

(22) PCT Filed: Apr. 26, 2002

(86) PCT No.: PCT/FR02/01450

§ 371 (c)(1),
(2), (4) Date: Oct. 27, 2003

(87) PCT Pub. No.: WO02/087575

PCT Pub. Date: Nov. 7, 2002

(65) Prior Publication Data

US 2004/0122036 A1  Jun. 24, 2004

(30) Foreign Application Priority Data

Apr. 27, 2001 (FR) .................................. 01 05843

(51) Int. Cl.
A61K 31/44 (2006.01)
(52) U.S. Cl. ..................................................... 514/292
(58) Field of Classification Search ................. 514/257, 514/292
See application file for complete search history.

(56) References Cited

U.S. PATENT DOCUMENTS

| | | | |
|---|---|---|---|
| 4,263,304 A | | 4/1981 | Ishizumi et al. |
| 4,835,160 A | | 5/1989 | Bisagni et al. |
| 5,035,252 A | * | 7/1991 | Mondre ...................... 132/321 |
| 5,880,126 A | | 3/1999 | Skuballa et al. |
| 6,486,177 B2 | * | 11/2002 | Zeldis et al. ................ 514/317 |
| 6,503,888 B1 | * | 1/2003 | Kaplitt et al. ................ 514/44 |
| 6,967,203 B2 | * | 11/2005 | Bourrie et al. ............... 514/257 |
| 2002/0156016 A1 | * | 10/2002 | Minuk .......................... 514/12 |
| 2007/0129365 A1 | | 6/2007 | Bourrie |

FOREIGN PATENT DOCUMENTS

| | | | |
|---|---|---|---|
| FR | 2003999 | | 11/1969 |
| FR | 2 765 581 | | 1/1999 |
| FR | 2765582 | | 1/1999 |
| FR | 9708409 | * | 1/1999 |
| IT | WO 01/09129 | * | 2/2001 |
| SU | 833971 | | 5/1981 |
| SU | 833972 | | 5/1981 |
| WO | WO99/51597 | | 10/1999 |
| WO | WO01/09129 | | 2/2001 |
| WO | WO2004/037821 | | 5/2004 |
| WO | WO2004/041817 | | 5/2004 |
| WO | WO2005/108398 | | 11/2005 |
| WO | WO2007/045758 A1 | | 4/2007 |

OTHER PUBLICATIONS

Goodman and Gilman Pharm. 9th Ed. Pharmacological Basis of Therapeutics (1996) pp. 1225-1232 and 1269-1271.*
Nicholson-Guthrie et al., Cancer Letters (2001), pp. 27-30.*
MayoClinic, last update Apr. 12, 2008, 11 pages.*
Derwent Patent Abstract No. 196800 (2003).
Derwent Patent Abstract No. 199909 (2003).
U.S. Appl. No. 10/476,322, filed Apr. 26, 2002, Bourrie et al.
Froissant et al., Derwent Patent Abstract No. 199909 (2003) (abstract of FR 2 765 581.
Furihata et al., In Vivo Short-Term Assays For Tumor Initiation And Promotion in the Grandular Stomach of Fischer Rats, Mutation Research, (1995), vol. 339, pp. 15-35.
Furihata et al., Unscheduled DNA Synthesis in Rat Stomach-Short-Term Assay of Potential Stomach Carcinogens, Banbury Report, (1982), vol. 13, pp. 123-135.
Goldman M.D., et al., Cecil, Textbook of Medicine, 21st edition, vol. 1, published 2000 by W.B. Saunders Co. (PA), pp. 1060-1074.
Golovko et al., A new Approach to the Synthesis of Functionally-Substituted Pyrido [2,3-d]indoles, Mendeleev Communications, (1995), vol. 6, pp. 226-227.
Molina et al., Annulation of Pyridine to Indole By a Tandem Aza-Wittig/Electrocyclization Strategy: Synthesis of Pyrido [2,3-b]indoles., Synthesis, (1989), vol. 11, pp. 878-880, Abstract No. 1982-25808e (XP-002184731, DW 198213) (1982).

* cited by examiner

*Primary Examiner*—Michael G Hartley
*Assistant Examiner*—Shirley V Gembeh
(74) *Attorney, Agent, or Firm*—Kelly L. Bender

(57) ABSTRACT

The invention relates to the combination of compounds of formula:

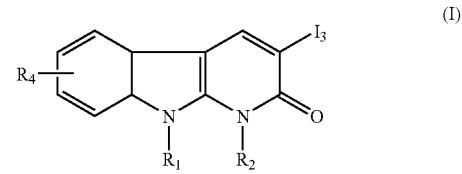

(I)

with one or more anticancer agents.

9 Claims, No Drawings

PHARMACEUTICAL COMBINATIONS BASED ON PYRIDOINDOLONE DERIVATIVES AND ANTICANCER AGENTS

The present invention relates to novel combinations of pyridoindolone derivatives with anticancer agents and the pharmaceutical compositions containing them.

The pyridoindolone derivatives which can be used in the present invention are the compounds of formula:

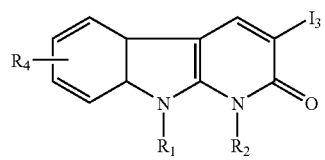

(I)

in which:
R$_1$ represents a hydrogen atom or a methyl or ethyl group;
R$_2$ represents a methyl or ethyl group; or
R$_1$ and R$_2$ together form a (CH$_2$)$_3$ group;
r$_3$ represents either a phenyl group optionally substituted with a halogen atom or a methyl or methoxy group, or a thienyl group;
R$_4$ represents a hydrogen or chlorine atom or a methyl or methoxy group.

It has been found that the compounds of formula (I), which are anticancer agents, can be advantageously combined with other anticancer agents.

Preferred pyridoindolone derivatives are the compounds of formula:

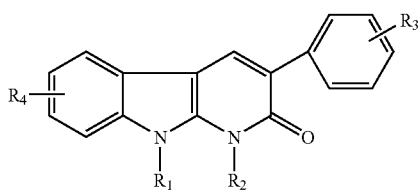

(Ia)

in which:
R$_1$ represents a hydrogen atom or a methyl or ethyl group;
R$_2$ represents a methyl or ethyl group; or
R$_1$ and R$_2$ together form a (CH$_2$)$_3$ group;
R$_3$ represents a hydrogen or halogen atom or a methyl or methoxy group;
R$_4$ represents a hydrogen or chlorine atom or a methyl or methoxy group.

Particularly preferred pyridoindolone derivatives are the compounds of formula:

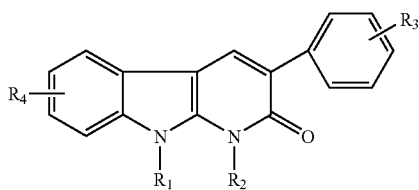

(Ia)

in which:
R$_1$ represents a hydrogen atom or a methyl or ethyl group;
R$_2$ represents a methyl or ethyl group;
R$_3$ represents a hydrogen or halogen atom or a methyl or methoxy group;
R$_4$ represents a hydrogen or chlorine atom or a methyl or methoxy group.

More particularly preferred pyridoindolone derivatives are the compounds of formula:

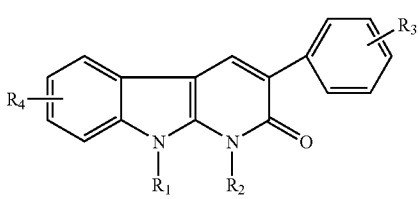

(Ia)

in which:
R$_1$ represents a methyl or ethyl group;
R$_2$ represents a methyl or ethyl group;
R$_3$ represents a hydrogen or halogen atom or a methyl or methoxy group;
R$_4$ represents a hydrogen or chlorine atom or a methyl or methoxy group.

By way of example, pyridoindolone derivatives according to the invention are:
6-chloro-1,9-dimethyl-3-phenyl-1,9-dihydro-2H-pyrido[2,3-b]indol-2-one; m.p.=178.5-179.5° C.;
3-(4-methoxyphenyl)-1,9-dimethyl-1,9-dihydro-2H-pyrido[2,3-b]indol-2-one; m.p. 166-167° C.;
1,6,9-trimethyl-3-(3-thienyl)-1,9-dihydro-2H-pyrido[2,3-b]indol-2-one;
NMR (200 MHz): 2.6 ppm: s: 3H; 4.1 ppm: s: 3H; 4.2 ppm: s: 3H; 7.1 ppm: d: 1H; 7.4-7.9 ppm: m: 4H; 8.3 ppm: d: 1H; 8.7 ppm: s: 1H.
1,6,9-trimethyl-3-phenyl-1,9-dihydro-2H-pyrido[2,3-b]indol-2-one; m.p. =198-199° C.;
1,6-dimethyl-3-phenyl-1,9-dihydro-2H-pyrido[2,3-b]indol-2-one;
NMR (200 MHz): 2.5 ppm: s: 3H; 3.8 ppm: s: 3H; 7.1 ppm: d: 1H; 7.3-7.5 ppm: m: 4H; 7;75 ppm: d: 2H; 7.8 ppm: s: 1H; 8.4 ppm: s: 1H; 11.8 ppm: s: 1H.

The compounds of formula (I) are prepared according to the process described in the document FR 97 08409.

The compounds of formula (I) were tested in vitro on a human breast cancer cell line: the line MDA-MB-231 available from the American Type Culture Collection (reference HTB26).

The assessment of the antiproliferative effect is carried out according to J. M. Derocq et al., FEBS Letters, 1998, 425, 419-425: the degree of incorporation of [3H]thymidine into the DNA of the treated cells is measured, after 96 hours of incubation of a compound of formula (I). The 50% inhibitory concentration (IC$_{50}$) is defined as the concentration that inhibits the cellular proliferation by 50%.

The compounds of formula (I) have an IC$_{50}$ value generally of less than 10 μM on the MDA-MB-231 line.

The compounds of formula (I) were also tested on another human breast cancer cell line, referred to as the multi-drug resistant MDR line and known as MDA-A$_1$. This line is described by E. Collomb, C. Dussert and P. M. Martin in Cytometry, 1991, 12(1), 15-25.

The term "multi-drug resistant" which qualifies this line means that the said line is generally relatively insensitive to the chemotherapy drugs commonly used and in particular to antimitotic agents of natural origin such as paclitaxel, vincristine and vinblastine.

The compounds of formula (I) have an $IC_{50}$ value that is generally less than 10 μM on the multi-drug resistant line $MDA-A_1$.

Thus the compounds of formula (I) inhibit the proliferation of tumor cells, including that of cells showing multi-drug resistance.

Several compounds of formula (I) were also assessed in vivo on a model of xenografting of human tumors implanted subcutaneously onto SCID (Severe Combined Immuno Deficiency) immunodeficient mice.

The treatment of the animals with a compound of formula (I) started 6 to 7 days after the implantation, when the tumor reached a tumoral mass of about 60 mg. The compound was then administered orally as a solution in a solvent.

The antitumor activity was assessed when the mean tumor mass reached about 1 000 mg in the control animals, treated with solvent alone: the T/C ratio was measured, T representing the mean weight of the tumors in the treated animals and C representing the mean weight of the tumors in the control animals. A T/C ratio of less than or equal to 42% is considered as indicating a significant antitumor activity according to Stuart T et al., in J. Med. Chem., 2001, 44 (11), 1758-1776. For an administered daily dose of between 50 and 300 mg/kg, certain compounds of formula (I) gave a T/C ratio of less than 20%.

The antiproliferative effects of the combination of a compound of formula (I) with another anticancer agent were measured on the $MDA-A_1$ line, the "multi-drug resistant" line referred to above, according to the referenced technique (J. M. Derocq et al.). The $IC_{50}$ value obtained for the anticancer agent alone was compared with that obtained for the combination of the same anticancer agent with a compound of formula (I). A marked decrease in the $IC_{50}$ value was observed. The $IC_{50}$ values can be divided by a factor ranging from 2 to 100 and even above 100 for certain pyridoindolone derivatives of formula (I) combined with another anticancer agent.

By way of example, the $IC_{50}$ value obtained for paclitaxel alone was compared with that obtained for the combination of paclitaxel with 1,6,9-trimethyl-3-phenyl-1,9-dihydro-2H-pyrido[2,3-b]indol-2-one. The $IC_{50}$ value is divided by a factor ranging from 14 to 100 depending on the concentrations of 1,6,9-trimethyl-3-phenyl-1,9-dihydro-2H-pyrido[2,3-b]indol-2-one used.

The results of the tests show a synergistic effect and potentiation of the antiproliferative effects of the components of the combinations of the invention.

According to the present invention, the compound(s) of formula (I) are administered in combination with one (or more) anticancer active principle(s). These active principles can be, in particular, antitumor compounds such as alkylating agents, alkyl sulfonates (busulfan), dacarbazine, procarbazine, nitrogen mustards (chlormethine, melphalan or chlorambucil), cyclophosphamide or ifosfamide; nitrosoureas such as carmustine, lomustine, semustine or streptozocin; antineoplastic alkaloids such as vincristine or vinblastine; taxanes such as paclitaxel; antineoplastic antibiotics such as actinomycin; intercalating agents; antineoplastic antimetabolites, folate antagonists, methotrexate; purine synthesis inhibitors; purine analogs such as mercaptopurine or 6-thioguanine; pyrimidine synthesis inhibitors, aromatase inhibitors, capecitabine, and pyrimidine analogs such as fluorouracil, gemcitabine, cytarabine and cytosine arabinoside; brequinar; anticancer hormonal agonists and antagonists including tamoxifen; kinase inhibitors, imatinib; growth factor inhibitors; some antiinflammatory agents which can be used in the treatment of cancer such as pentosane polysulfate, corticosteroids, prednisone or dexamethasone; anti-topoisomerases such as etoposide, antracyclines including doxorubicin, bleomycin, mitomycin and methramycin; anticancer metallic complexes, platinum complexes, cisplatin, carboplatin or oxaliplatin; alpha-interferon, triphenylthio-phosphoramide or altretamine; anti-angiogenic agents; immunotherapy adjuvants.

The combinations of the invention are useful for the prevention and treatment of diseases caused or exacerbated by the proliferation of tumor cells, such as primary or metastatic tumors, carcinomas and cancers, in particular: breast cancer; lung cancer; cancer of the small intestine, cancer of the colon and of the rectum; cancer of the respiratory pathways, of the oropharynx and of the hypopharynx; cancer of the esophagus; liver cancer, stomach cancer, cancer of the bile ducts; cancer of the bile vesicle, cancer of the pancreas; cancers of the urinary pathways including the kidneys and the urothelium, cancer of the bladder; cancers of the female genital tract including cancer of the uterus, of the cervix and of the ovaries, chloriocarcinoma and trophoblastoma; cancers of the male genital tract including cancer of the prostate, of the seminal vesicles and of the testicles, and tumors of the germinal cells; cancers of the endocrine glands including cancer of the thyroid, of the pituitary and of the adrenal glands; skin cancers, including hemangiomas, melanomas and sarcomas, including Kaposi's sarcoma; tumors of the brain, of the nerves, of the eyes, of the meninges, including astrocytomas, gliomas, glioblastomas, retinoblastomas, neurinomas, neuroblastomas, schwannomas and meningiomas; tumors arising from hematopoietic malignant tumors including leukemias, chloromas, plasmacytomas, fungoid mycosis, lymphoma or T cell leukemia, non-Hodgkin lymphoma, malignant hemopathies and myelomas.

A subject of the present invention is also pharmaceutical compositions containing, as active principle(s), a therapeutically effective amount of at least one compound of formula (I), or a pharmaceutically acceptable salt, a hydrate or a solvate of the said compound, and a therapeutically effective amount of one (or more) other anticancer active principle(s), and also one or more pharmaceutically acceptable excipients.

The said excipients are chosen, according to the pharmaceutical form and the desired mode of administration, from the usual excipients that are known in the prior art.

The pharmaceutical compositions of the present invention may be prepared for oral, sublingual, subcutaneous, intramuscular, intravenous, topical, local, intratracheal, intranasal, transdermal or rectal administration, or for administration via any other suitable route, to man and animals for the prevention or treatment of the above diseases.

The compounds of formula (I) above may be used at daily doses of from 0.002 to 2 000 mg per kilogram of bodyweight of the mammal to be treated, preferably at daily doses of from 0.1 to 300 mg/kg. In man, the dose may preferably range from 0.02 to 10 000 mg per day and more particularly from 1 to 3 000 mg depending on the age of the individual to be treated or the type of treatment (prophylactic or curative).

The anticancer active principles with which the compounds of formula (I) are combined are used at the usual doses.

The suitable administration forms comprise oral forms such as tablets, soft or hard gel capsules, powders, granules and oral solutions or suspensions, sublingual, buccal, intratracheal, intraocular, intranasal or inhaled administration forms, topical, transdermal, subcutaneous, intramuscular or intravenous administration forms, rectal administration forms and implants. For topical application, the combinations of the invention may be used in creams, gels, ointments or lotions.

According to the usual practice, the dosage that is suitable for each patient is determined by the doctor according to the mode of administration, the age, the weight and the response of the said patient.

According to another aspect of the invention, the compound(s) of formula (I) and one (or more) other anticancer active principle(s) may be administered simultaneously, sequentially or separately over time, for the treatment of diseases caused or exacerbated by the proliferation of tumor cells.

The combinations of the invention may be in the form of a kit containing, firstly, at least one compound of formula (I) and, secondly, one (or more) other anticancer active principle (s).

According to another of its aspects, the invention also relates to a method for treating diseases caused or exacerbated by proliferation of tumor cells, which consists in administering to an individual in need thereof a therapeutically effective amount of at least one compound of formula (I) in combination with one (or more) other anticancer active principle(s).

What is claimed is:

1. A method for treating a disease caused or exacerbated by the proliferation of tumor cells which comprises administering to a patient having said disease and in need of such treatment an effective amount of at least one compound of formula:

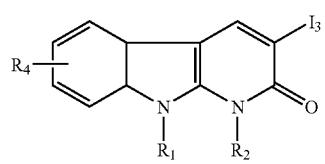

(I)

in which:
R$_1$ represents a hydrogen atom or a methyl or ethyl group;
R$_2$ represents a methyl or ethyl group; or
R$_1$ and R$_2$ together form a (CH$_2$)$_3$ group;
r$_3$ represents either a phenyl group optionally substituted with a halogen atom or a methyl or methoxy group, or a thienyl group;
R$_4$ represents a hydrogen or chlorine atom or a methyl or methoxy group;
or a pharmaceutically acceptable salt, hydrate or solvate thereof;
in combination with one or more anticancer active principle(s) selected from alkylating agents, alkyl sulfonates, dacarbazine, procarbazine, nitrogen mustards, cyclophosphamide, ifosfamide, nitrosoureas, antineoplastic alkaloids, taxanes, antineoplastic antibiotics, intercalating agents, antineoplastic antimetabolites, folate antagonists, methotrexate, mercaptopurine, 6-thioguanine, aromatase inhibitors, capecitabine, fluorouracil, gemcitabine, cytarabine, cytosine arabinoside, brequinar, tamoxifen, kinase inhibitors, imatinib; growth factor inhibitors, antiinflammatory agents which can be used in the treatment of cancer, anti-topoisomerases, antracyclines, anticancer metallic complexes, platinum complexes, alpha-interferon, triphenylthio-phosphoramide, altretamine; anti-angiogenic agents, and immunotherapy adjuvants;
wherein said disease is selected from the group consisting of breast cancer; lung cancer; cancer of the small intestine; cancer of the colon; cancer of the rectum; cancer of the respiratory pathways; cancer of the oropharynx; cancer of the hypopharynx; cancer of the esophagus; liver cancer; stomach cancer; cancer of the bile ducts; cancer of the bile vesicle; cancer of the pancreas; cancers of the urinary pathways; cancer of the bladder; cancers of the female genital tract; cancers of the male genital tract; cancers of the endocrine glands; skin cancers; tumors of the brain, tumors of the nerves, tumors of the eyes, tumors of the meninges; and tumors arising from hematopoietic malignant tumors.

2. The method as claimed in claim 1 which comprises administering at least one compound of formula:

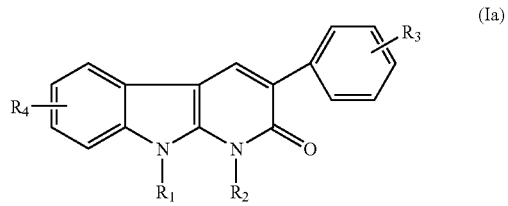

(Ia)

in which:
R$_1$ represents a hydrogen atom or a methyl or ethyl group;
R$_2$ represents a methyl or ethyl group; or
R$_1$ and R$_2$ together form a (CH$_2$)$_3$ group;
R$_3$ represents a hydrogen or halogen atom or a methyl or methoxy group;
R$_4$ represents a hydrogen or chlorine atom or a methyl or methoxy group;
or a pharmaceutically acceptable salt, hydrate or solvate thereof.

3. The method as claimed in claim 1 which comprises administering at least one compound of formula:

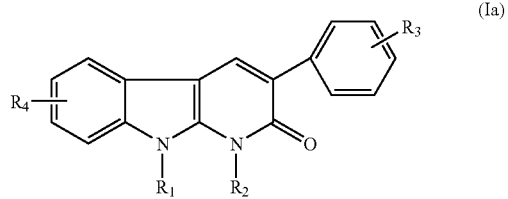

(Ia)

in which:
R$_1$ represents a hycwogen atom or a methyl or ethyl group;
R$_2$ represents a methyl or ethyl group;
R$_3$ represents a hydrogen or halogen atom or a methyl or methoxy group;
R$_4$ represents a hydrogen or chlorine atom or a methyl or methoxy group;
or a pharmaceutically acceptable salt, hydrate or solvate thereof.

4. The method as claimed in claim 1, in which the compound of formula (I) is:
6-chloro-1,9-dimethyl-3-phenyl-1,9-dihydro-2H-pyrido [2,3-b]indol-2-one;
3-(4-methoxyphenyl)-1,9-dimethyl-1,9-dihydro-2H-pyrido[2,3-b]indol-2-one;

1,6,9-trimethyl-3-(3-thienyl)-1,9-dihydro-2H-pyrido[2,3-b]indol-2-one;

1,6,9-trimethyl-3-phenyl-1,9-dihydro-2H-pyrido[2,3-b]indol-2-one; or 1,6-dimethyl-3-phenyl-1,9-dihydro-2H-pyrido[2,3-b]indol-2-one;

or a pharmaceutically acceptable salt, hydrate or solvate thereof.

5. A method as claimed in claim 1 which comprises administering at least one compound of formula:

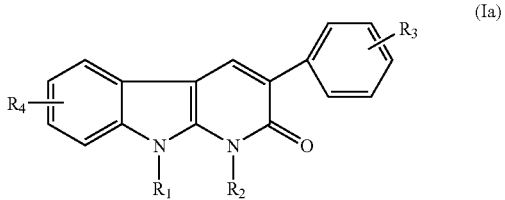

in which:
R$_1$ represents a methyl or ethyl group;
R$_2$ represents a methyl or ethyl group;
R$_3$ represents a hydrogen or halogen atom or a methyl or methoxy group;
R$_4$ represents a hydrogen or chlorine atom or a methyl or methoxy group;

or a pharmaceutically acceptable salt, hydrate or solvate thereof.

6. The method according to claim 1 wherein the compound of formula (I) and the one or more anticancer active principle(s) are administered simultaneously, sequentially, or separately over time.

7. The method according to claim 1, wherein the disease is selected from the group consisting of breast cancer, lung cancer, cancer of the colon, cancers of the male genital tract, skin cancers, and tumors of the brain.

8. The method according to claim 1, wherein the one or more anticancer active principle(s) is selected from busulfan, dacarbazine, procarbazine, chlormethine, melphalan, chlorambucil, cyclophosphamide, ifosfamide, carmustine, lomustine, semustine, streptozocin, vincristine, vinblastine, paclitaxel, actinomycin, methotrexate, mercaptopurine, 6-thioguanine, capecitabine, fluorouracil, gemcitabine, cytarabine, cytosine arabinoside, brequinar, tamoxifen, imatinib, pentosane polysulfate, prednisone, dexamethasone, etoposide, doxorubicin, bleomycin, mitomycin, methramycin, cisplatin, carboplatin, oxaliplatin, alpha-interferon, triphenylthiophosphoramide, and altretamine.

9. The method according to claim 1, wherein the one or more anticancer active principle(s) is selected from antineoplastic alkaloids and platinum complexes.

* * * * *

UNITED STATES PATENT AND TRADEMARK OFFICE
CERTIFICATE OF CORRECTION

PATENT NO. : 7,524,857 B2  
APPLICATION NO. : 10/476321  
DATED : April 28, 2009  
INVENTOR(S) : Bernard Bourrie et al.

It is certified that error appears in the above-identified patent and that said Letters Patent is hereby corrected as shown below:

On the face page, in field (57), under "Abstract" in column 2, line 1, Structure I, delete

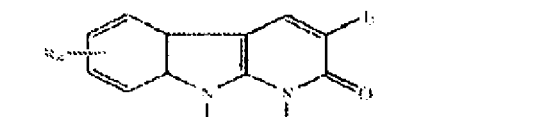 " and insert -- 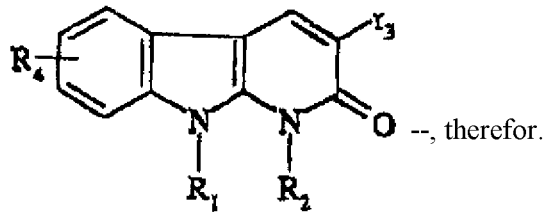 --, therefor.

In column 1, line 10-19, delete " 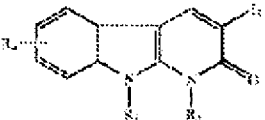 " and insert

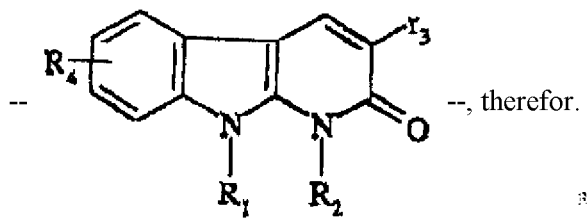 --, therefor.

In column 5, line 33-40, in Claim 1, delete "  " and insert

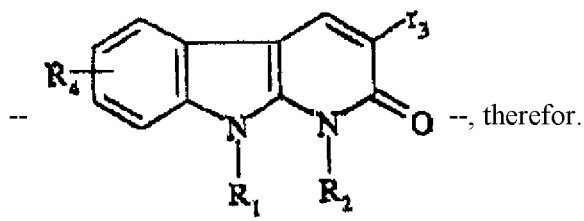 --, therefor.

In column 6, line 54, in Claim 3, delete "hycwogen" and insert -- hydrogen --, therefor.

Signed and Sealed this

Sixth Day of July, 2010

David J. Kappos  
*Director of the United States Patent and Trademark Office*